(12) United States Patent
Sawhill

(10) Patent No.: US 6,787,168 B1
(45) Date of Patent: Sep. 7, 2004

(54) PEPTIDE PRODUCT

(76) Inventor: James W. Sawhill, 1403 Rampart Dr., Roseville, CA (US) 95661

( * ) Notice: Subject to any disclaimer, the term of this patent is extended or adjusted under 35 U.S.C. 154(b) by 0 days.

(21) Appl. No.: 10/249,130

(22) Filed: Mar. 18, 2003

(51) Int. Cl.$^7$ .............................. C12P 21/06; A23J 3/34; A23J 3/08

(52) U.S. Cl. ........................... 426/41; 426/42; 426/583; 530/343; 435/68.1

(58) Field of Search .............................. 426/46, 41, 42, 426/34, 52, 56, 18, 590, 583, 656; 435/68.1; 830/343; 530/360, 365

(56) References Cited

U.S. PATENT DOCUMENTS

| | | | | |
|---|---|---|---|---|
| 5,618,689 A | * | 4/1997 | McCarthy et al. | 435/68.1 |
| 6,022,567 A | * | 2/2000 | Lecouteux et al. | 426/35 |
| 6,024,990 A | * | 2/2000 | Kofoed et al. | 426/44 |
| 6,372,282 B1 | * | 4/2002 | Edens et al. | 426/656 |
| 6,372,452 B1 | * | 4/2002 | Millan Rodriguez et al. | 435/68.1 |
| 6,451,359 B1 | * | 9/2002 | Nsofor | 426/46 |
| 6,620,778 B2 | * | 9/2003 | Mallee et al. | 514/2 |
| 6,669,972 B2 | * | 12/2003 | Blortz et al. | 426/52 |

FOREIGN PATENT DOCUMENTS

| WO | WO/25580 | * 11/1994 | ............ C12N/9/62 |
|---|---|---|---|

* cited by examiner

*Primary Examiner*—Keith Hendricks
(74) *Attorney, Agent, or Firm*—Richard D. Fuerle

(57) ABSTRACT a peptide product is made by enzymatically hydrolyzing a protein, such as whey protein concentrate, in two stages. A fungal protease is used to hydrolyze the protein in each stage. The hydrolyzed protein is dried to form a peptide product. The peptide product is non-allergenic and lacks the bitter taste that some other peptide products have. If can be used to make milk replacement products and various other food products.

18 Claims, No Drawings

PEPTIDE PRODUCT

BACKGROUND OF INVENTION

This invention relates to a peptide product and to a method of making it by hydrolyzing protein. In particular, it relates to a two-stage enzymatic hydrolysis of whey protein concentrate using fungal enzymes to produce a peptide product that can be used to make a milk replacement and as a component in other food products.

Because many people are allergic to the proteins that are in milk, milk proteins need to be broken down into non-allergenic peptides before they are used in food products. It is necessary to break down almost all of the allergic proteins since only a small amount of the intact protein can cause the reaction. However, it is difficult to break down some of the proteins in milk and even low concentrations of certain proteins in a food product can cause allergic reactions in some people. Also, during the process of converting the milk proteins into peptides various bitter-tasting or off-tasting products can be formed. These bad tastes are difficult or impossible to remove and can be so strong that they cannot be hidden by the addition of sugar or flavors. Also, products that leave various after-tastes can also be formed. Some products have an unacceptably high bacterial count and/or a low protein efficiency ratio (PER, which is a measure of the effectiveness of the protein in adding mass to a rat). Some of the recent past published procedures called for fractionating the bitter peptides into two fractions. Some of these fractions were not bitter. Unfortunately, these fractions seemed to be very high in non-essential amino acids. To use these non-bitter fractions called for supplementation with several essential amino acids (Cordle). Since those amino acids are nutritionally important, the resulting product is nutritionally deficient. If the product has a dark color, that may also be unacceptable for use in light-colored products.

At the present time there are no commercially available peptide products that meet all these often-conflicting requirements.

SUMMARY OF THE INVENTION

In the process of this invention, a protein source is digested (hydrolyzed) in two stages using fungal enzymes, then dried to produce a mixture of peptides and free amino acids. Unlike some of the peptide products produced by other methods, the peptide product of the method of this invention retains the full nutritional value of the protein from which it was made. Also, it has essentially no non-diary flavor and does not have a bitter taste or an after taste. Because all of the allergy-causing proteins are broken down into peptides and amino acids in the process of this invention, the product is non-allergenic. It is light-colored and can be easily substituted for milk protein in various food products.

DETAILED DESCRIPTION

Any type of protein can be used as the starting material in this invention, but it is best to start the enzymatic digestion with either a soluble protein solution or a homogenized protein solution of an animal or vegetable tissue. There are, for example, several soluble isolates of soy that can be used as a substrate and all the milk proteins, such as casein and the whey proteins, can be used. The whey proteins can be separated into their component proteins and each will be easily digested by the procedure of this invention. Casein, which is made from milk, and soy protein, which comes from soybeans, are not preferred because casein is more expensive and has a less desirable amino acid profile and soy protein has lower nutritional values. The preferred protein is whey, the liquid that remains after the removal of the cheese curds, the remaining liquid by-product, on an anhydrous basis is typically about 14% protein, about 70% lactose, and the remainder milk minerals.

Whey is obtained as a by-product of the manufacturing of cheese; it is that portion of the milk that is not in the cheese. Whey is a solution that leaves the cheese vats after the cheese solids (about 10%) have been removed. After the removal of the cheese, whey is about 6 to about 8 wt % solids, but it can be concentrated under vacuum to about 40 wt % dissolved solids. To prepare a dried product from whey, water is evaporated under vacuum and the product is dried. The dried product has a variety of uses, including as cattle feed and as a source of lactose, and also as a diluent in the manufacture of pills.

Whey protein concentrate (WPC) is the high protein fraction of the whey. It is made from the whole whey solution by passing the solution through a membrane that retains larger molecules but permits smaller molecules to pass through. The lactose and phosphates pass through the membrane, but the proteins don't. The retained protein fraction from the membrane step is concentrated to about 40 wt % and is spray dried to form WPC. The WPC is sold according to the percentage of protein in it, i.e., WPC 65 is 65 wt % protein, WPC 80 is 80 wt % protein, etc., with the remainder being the other solid components in the milk, such as lactose, butterfat, and ash. While WPC with any percentage of protein in it can be used, a WPC having about 65 to about 80 wt % protein is preferred because at lower percentages of protein and higher percentages of lactose, it is difficult to maintain a white color during the enzymatic digestion step. There are some WPC 100's available, but they are more expensive due to the difficulties of removing the remaining 20 wt % contaminants present in the WPC 80 preparations. There are two main protein fractions in the protein mixtures in whey. The smallest in size is about 180 amino acids long and the large one is about 350 amino acids long.

In the first step of the process of this invention, the protein is hydrolyzed. Enzymatic hydrolysis is the process of splitting the peptide bond of a protein in an aqueous solution. When a peptide bond is broken, one alpha amino group and one carboxyl acid group are formed. For best results, the protein to be hydrolyzed should be at a temperature of about 80 to about 120° F. At lower temperatures the reaction slows down and considerably more time is required to achieve sufficient digestion. Also, there is the real possibility of bacterial spoilage before the DH (degree of hydrolyzation) reaches levels adequate to insure that the product is non-antigenic. For every 18 degrees decrease in temperature during the enzymatic digestion the reaction rate falls by half. This digestion is a first order chemical reaction, so it is very temperature sensitive. The preferred temperature range is about 100 to about 115° F.

The protein is hydrolyzed as an aqueous solution at a concentration of about 5 to about 20 wt %. The maximum rate of hydrolysis is achieved when the protein concentration is between about 8 and about 10 wt %. Lower percentages of protein require considerably more enzyme to reach the same digestion achieved with an 8 to 10 wt % protein level.

A protease (also, "proteinase"), an enzyme that hydrolyzes protein, is used to catalyze the hydrolyzation of the protein. The protease used greatly affects the quality of the resulting peptide product. Proteases from bacteria should not be used as the digested WPC has an unacceptable bitter taste when those proteases are used. Proteases from plants and animals should also not be used as they produce an off-flavor in the digested WPC. That is, the flavor may not be bad-tasting, but it is a different flavor than the WPC had. After a great deal of experimentation, it has been determined that proteases prepared from fungi are effective and do not produce a peptide product that has a bitter taste or an off-flavor. Each fungal protease is actually a mixture of various enzymes that are believed to be structurally closely related, though the actual structure of each enzyme in the mixture and its proportion in the mixture have not yet been determined. Examples of suitable fungal proteases include "Flavourzyme," (sold by Novo) from the fungus *Aspergillus oryzae* and "Fungal Protease 500,000" and "Fungal Protease Concentrate," (sold by Genencor) from *Aspergillus oryzae*. The preferred fungal proteases are Flavourzyme and Fungal Protease 500,000 because they are more effective in the first hydrolyzation. While the same protease can be used in both the first and the second hydrolyzations, it is usually preferably to use different proteases because they seem to give a higher DH after the full two step digestion period. Also, Fungal Protease Concentrate is best used only in the second hydrolyzation.

In the first enzymatic hydrolyzation, the protein is mixed with about 0.01% to about 1 wt % (based on total composition weight) of a fungal protease. More fungal protease may not produce a proportional increase in DH and less fungal protease may not increase the DH to the required percentage. The preferred amount of fungal protease is about 0.05 to about 0.3 wt %. The mixture is stirred and is monitored by high pressure liquid chromatography (HPLC) to determine the percentage of the protein that has been hydrolyzed. The DH at the end of the first digestion step can vary from about 16 to about 25%. If less protein is hydrolyzed, it may be difficult to hydrolyze all the remaining protein molecules in the second enzymatic hydrolyzation. The DH gives the percentage of the amino acid linkages that have been broken. For example, a DH of 25% means that 25% of the amino acid linkages have been broken, forming basic amine groups and acidic carboxylic acid groups. The DH is obtained by titration—measuring the amount of base needed to raise the pH to 8. Preferably, about 20 to about 25 wt % of the protein is hydrolyzed in the first enzymatic hydrolyzation. The first enzymatic hydrolyzation should be permitted to continue until the rate of hydrolyzation falls significantly. This can be determined by monitoring the DH, but it is usually convenient to simply run the first hydrolyzation for 24 hours even though in many cases a sufficiently high DH may be achieved in less time. The time for the first digestion can vary as needed, but about 24 to about 48 hours is usually adequate.

In the second digestion step, the DH will increase to about 25 to about 33%. During the first hydrolyzation, the pH is permitted to drift and it will gradually fall because the carboxylic acid groups being formed are more acidic than the amine groups being formed are basic. As the pH falls, bacteriostatic peptides are formed, which keep the bacterial count low. A pH below 5 is needed to control bacteria. Normally, the digestion process itself will reduce the pH to below 5, but if it fails to do so, a non-buffering acid, such as sulfuric acid or hydrochloric acid can be added.

It has been found that a single enzymatic hydrolyzation is unsatisfactory because in a single hydrolyzation it is difficult to obtain a DH that is high enough to ensure that all of the proteins present have been hydrolyzed. While extra protease could be used in the first hydrolyzation to obtain a higher DH, that typically requires more time and more protease than using a second digestion. The reason that a second digestion works better than a prolonged first digestion may be that the protease is itself a protein and therefore protease molecules attack other protease molecules. This useless loss of protease can be reduced if the concentration of protease is lower, as it is when two digestions are used. For these reasons, the process of this invention requires at least two enzymatic hydrolyzations. While 3 or more hydrolyzations could be used, preferably only two are used as that is usually adequate to achieve the desired DH. In the second digestion about 0.01 to about 1 wt % of additional fungal protease is added, preferably about 0.05 to about 0.3 wt %. The DH increase is less in the second digestion as less protein is present to be digested. While it is usually convenient to permit the second digestion to run for 24 hours, it can be terminated sooner if the DH has reached an acceptable level. The time for the second digestion can vary as needed, but about 24 to about 48 hours is usually adequate.

After the second enzymatic hydrolysis, the DH should be between about 22 and about 40. As a general rule, it is better to have a DH over about 18. Allergic reactions due to protein are more likely to happen with a low DH. Therefore, a high DH is best to insure non-allergic peptides. However, a DH higher than about 40 may alter the taste as the proportion of amino acids to peptides may be too high. Preferably, the DH Is about 23 to about 35 after the second digestion.

The pH of the peptide product should be in a range that is suitable for use as a food, preferably a pH of about 6.5 to about 7.0. Since the pH will normally be below that range, it will usually be necessary to raise the pH by the addition of a base. Any base that is GRAS (generally regarded as safe), such as sodium hydroxide, can be use to raise the pH. A 50 wt % solution of sodium hydroxide is preferred for use in adjusting the pH. Of course, if the pH is already within the desired range, no pH adjustment will be necessary.

After the pH adjustment, if any, the peptide product is dried. Drying can be accomplished by spray drying, freeze drying, or vacuum drum drying, but it is preferably done by spray drying as that method is less expensive and does not damage the peptide product.

Optionally, mechanical deodorization can be performed on the peptide product to remove volatiles that may be malodorous. Mechanical deodorization is accomplished by passing the solution slowly through a thin film evaporator while the unit is under vacuum.

The peptide product is a readily water-soluble white or light cream colored solid in the form of a powder or granules. It is a mixture of large and small peptides and free amino acids. None of the amino acids that are present in the starting protein are lost in the process of this invention and they are all present in the peptide product, either in peptides or as free amino acids. In taste tests using trained human tasters, the product of this Invention was described as having no bitter taste. Also, the in vitro test called "ELISA" gives an antigenicity number, which is an indication of the antigenic qualities of a protein. In U.S. Pat. No. 5,837,312, the antigenic qualities of both casein and whey casein were compared before and after the enzymatic digestion to a DH of 18%. The whey protein antigenicity number was lowered from 78,000 to 760 units, a 99% removal of antigenicity factor. Peptide products having a higher DH will have an even lower antigenicity factor.

A milk replacement product can be made from the peptide product by replacing the protein component in milk with the peptide product of this invention. For example, if the milk is about 3 wt % protein, the protein can be removed from the milk and replaced with about 3 wt % of the peptide product of this invention. Alternatively, a milk replacement product could be formulated from a variety of components to simulate the milk of different mammals. For example, cow's milk typically is about 7 wt % lactose, 3 wt % butterfat, 3 wt % protein, and the remainder water. A cow's milk replacement could be made, for example, with a composition of about 4 to about 10 wt % of a carbohydrate, about 1 to about 5 wt % of a fat, and about 1 to about 5 wt % of the peptide product of this invention. Since some people are lactose-intolerant, another carbohydrate, such as sucrose, corn syrup, or maltose, could be used instead of lactose. To satisfy vegetarians or people who want to avoid butterfat for medical reasons, soy oil or a hard fat such as tallow could be used instead. If desired, food dyes, flavoring agents, preservatives, and other components can be added to the milk replacement, as is known in the art. Because the peptide product will spoil once it has been added to water, a preservative may be added to aqueous compositions containing it to reduce bacterial spoilage.

A number of experiments were performed which further illustrate this invention. Unless otherwise noted, all of these experiments used the following standard operating procedure (SOP): A 10 wt % aqueous solution of a WPC 80 was prepared and the temperature of the solution was raised to 105° F. with stirring. To the solution was added 0.1 wt % of a protease with stirring and the mixture was permitted to digest for 24 hours at that temperature. During that first digestion, the pH and DH was determined every 6 hours. After the first 24 hour digestion, 0.1 wt % of a second protease was added and the digestion was continued for an additional 24 hours at the same temperature, again determining the pH and DH every 6 hours. The solution was then heated to 145° F. with stirring for 30 minutes to pasteurize it. The solution was passed through a thin film evaporator using 20 inches of vacuum at a rate of 1 gallon per minute. It was then neutralized to a pH of 6.5 to 7.0 with a 50 wt % solution of sodium hydroxide. The solution was spray dried and samples were taken for taste tasting and to determine bacterial count. No change in the color of the peptide product over the color of the WPC was noted in any of the experiments. The following examples describe these experiments:

EXAMPLE 1

The DH rates at five different substrate concentrations were determined using 0.1 wt % Flavourzyme. The following table gives the results:

| Sample | Wt % | 16 hour DH (%) | 48 hour DH (%) |
|--------|------|----------------|----------------|
| 1 | 6 | 15 | 24 |
| 2 | 8 | 14 | 25 |
| 3 | 10 | 15 | 22 |
| 4 | 14 | 12 | 20 |
| 5 | 16 | 10 | 16 |

The enzyme seemed to be active throughout the 48 hour period. The rate of increase in DH fell off after the first 16 hours but was still increasing at about half the earlier rate. Boiling the neutralized finished product resulted in the precipitation of protein. There were no signs of spoilage. The finished product had an acceptable odor and tasted cheesy. The experiments show that to achieve maximum digestion it is better to have the whey protein concentration at 10 wt % or less.

EXAMPLE 2

Example, the pH, DH, taste, and DH per hour were followed on a Flavourzyme digestion over 48 hours. Into a flask equipped with a magnetic stirrer was placed 500 ml of a 10 wt % aqueous solution of WPC 80 sold by LePrimo, 0.1 wt % (i.e., 1 ml per liter of solution) of potassium sorbate, and 0.1 wt % Flavourzyme. The flask was placed in a forced air oven at 110° F. and held at that temperature for 48 hours. Initially and every 8 hours thereafter the pH and DH of the solution were determined and a sample was removed and tested for taste by a skilled human taster. At the end of the experiment, 100 ml of the solution was checked for stability and to determine if the protease was still working. The remainder was boiled to precipitate any remaining protein. The following table gives the results.

| Sample | pH | DH (%) | Taste | Hours | DH (% increase/hr) |
|--------|-----|--------|-------|-------|---------------------|
| 1 | 6.3 | 3 | OK | 0 | 0.0 |
| 2 | 5.8 | 9 | OK | 8 | 0.75 |
| 3 | 5.3 | 13 | OK | 16 | 0.8 |
| 4 | 5.0 | 19 | OK | 24 | 0.4 |
| 5 | 4.0 | 22 | OK | 32 | 0.3 |
| 6 | 3.8 | 29 | OK | 48 | 0.4 |

The pH dropped from 6.3 to 3.8 during the digestion period, there was no sign of spoilage, and the DH per hour increased over the entire 48 hours, indicating the enzyme was still active.

EXAMPLE 3

The purpose of this example was to determine the DH, pH, and tastes of nine combinations of three different fungal enzymes.

A 1500 ml solution was made of 10 wt % WPC 80 sold by LePrimo. The solution was split into 3 equal parts and 0.1 wt % of one of the three enzymes to be tested was added to each part. The 3 solutions were stirred and were permitted to digest overnight at 105° F. The pH and DH were determined at 12 hours and 24 hours. The following table gives the results:

| | Protease used | | At 12 hours | | At 24 hours | |
|--------|---------------|--------|-------------|--------|-------------|--------|
| Sample | First | Second | pH | DH (%) | pH | DH (%) |
| 1 | Flavourzyme | None | 5.2 | 18 | 4.3 | 24 |
| 2 | Fungal Protease 500,000 | None | 4.8 | 18 | 4.2 | 24 |
| 3 | Fungal Protease Concentrate | None | 5.2 | 19 | 5.2 | 8 |
| 4 | Flavourzyme | Flavourzyme | 3.6 | 30 | 4.4 | 38 |
| 5 | Flavourzyme | Fungal Protease 500,000 | 3.7 | 30 | 4.3 | 25 |
| 6 | Flavourzyme | Fungal Protease Concentrate | 3.8 | 26 | 4.3 | 27 |
| 7 | Fungal Protease 500,000 | Flavourzyme | | | 4.5 | 31 |

-continued

| Sample | Protease used First | Second | At 12 hours pH | DH (%) | At 24 hours pH | DH (%) |
|---|---|---|---|---|---|---|
| 8 | Fungal Protease 500,000 | Fungal Protease 500,000 | | | 4.7 | 32 |
| 9 | Fungal Protease 500,000 | Fungal Protease Concentrate | | | 4.8 | 28 |
| 10 | Fungal Protease Concentrate | Flavourzyme | | | 6.2 | 9 |
| 11 | Fungal Protease Concentrate | Fungal Protease | | | 6.2 | 9 |
| 12 | Fungal Protease Concentrate | Fungal Protease Concentrate | | | 6.2 | 9 |

Fungal concentrate did not work well when it was the first enzyme and samples 10, 11, and 12 were not acceptable; the apparent decrease in DH may have been due to bacteria.

The first six samples were tasted in a 5 wt % solution and by making a milk replacement and tasting it. The tasting was performed by a trained human taster. The six laboratory preparations were each compared to two controls. The first control was the parent WPC used in the enzymatic digestions and the second control was a pilot batch where Flavourzyme was used in both digestions that had been through a seven step pilot production and had previously tasted very similar to the parent WPC. The taster concluded that all six milk formulation were very similar and there were only minute differences between them. The taster rated the samples as follows:

| Sample | Taste | DH (%/24 hrs) | DH (%/48 hrs) |
|---|---|---|---|
| 4 | 2nd best | 24 | 27 |
| 5 | Best | 24 | 28 |
| 6 | 2nd best | 24 | 25 |
| 7 | 3rd best | 24 | 31 |
| 8 | 3rd best | 24 | 32 |
| 9 | 5th best | 24 | 28 |

The difference between the taste of the samples was not detectable once they had been made into a milk replacement with the formula of 7 wt % lactose, 3 wt % butterfat, 3 wt % peptides, and the remainder water.

EXAMPLE 4

In this Example, four different sources of WPC were tested to see how they would respond to an SOP digestion over 48 hours using both Fungal Protease 500,000 and Flavourzyme. Into a flask was placed 400 ml of WPC 80 sold by LePrimo to which was added 0.1 wt % Flavourzyme. The solutions were permitted to digest for 24 hours, then an additional 0.1 wt % of either Flavourzyme or Fungal Protease 500,000 was added and digestion was permitted to continue for a second 24 hours. The following table gives the WPCs and proteases tested and the results:

| Sample | WPC | 24 hr pH | 24 hr DH (%) | 24 hr taste | 48 hr pH | 48 hr DH (%) | 48 hr taste |
|---|---|---|---|---|---|---|---|
| | | | | | Using Flavourzyme | | |
| 1 | Protient 80 | 5.9 | 9.5 | ??? | 5.2 | 15 | OK |
| 2 | Davisco 80 | 5.0 | 12 | OK | 4.9 | 18 | OK |
| 3 | LOL 100 | 4.8 | 12 | OK | 4.8 | 20 | OK |
| 4 | La Primo 80 | 4.4 | 20.0 | OK | 4.3 | 25 | OK |
| | | | | | Using Fungal Protease 500,000 | | |
| 1 | Protient 70 | 5.0 | 9.5 | ??? | 5.2 | 20 | OK |
| 2 | Davisco 80 | 5.0 | 12 | OK | 4.6 | 20 | OK |
| 5 | LOL 100 | 4.8 | 12 | OK | 4.6 | 25 | OK |
| 6 | La Primo 80 | 4.4 | 20 | OK | 4.4 | 34 | OK |

The experiment showed that the best WPC was LePrimo 80, the second best was LOL 100, and there was not much difference between Protient 70 and Davisco 80. Only LePrimo 80 was acceptable in this experiment because the DH of the samples that used the other proteases was too low after 48 hours. The Protient 80 samples went from opaque to clear in the first 12 hours of digestion. At 12 hours the pH of the Protient 80 samples had dropped to 6 where it remained after 24 hours. There were signs of spoilage in the Protient 80 samples.

EXAMPLE 5

In this Example, samples were evaluated bacteriologically at two temperatures. Into a flask was dissolved 60 g WPC 80 sold by LePrimo in 540 ml water and the temperature of the solution was raised to 112° F. Two samples of 100 ml each were removed from the solution to use as controls. To the remaining solution was added 0.4 ml Flavourzyme and the solution was permitted to digest for 24 hours. After 24 hours, two 100 ml samples were again taken for testing. To the remaining solution was added 0.2 ml Flavourzyme and the solution was permitted to digest for and additional 24 hours, then split into two samples. One sample of the control, the 24 hour digestion, and the 48 hour digestion was stored at room temperature and the other sample of the control, the 24 hour digestion, and the 48 hour digestion was placed in an incubator at 110° F. The following table gives the bacterial count of the samples:

| Sample | Description | Temperature | pH | DH (%) | Bacterial count/ml |
|--------|-------------|-------------|-----|--------|--------------------|
| 1-0 | No enzyme | Ambient | 6.3 | 3 | 10,000 |
|  | No enzyme | 100° F. | 6.3 | 3 | 10,000 |
| 1-1 | 24 hr Flavourzyme | Ambient | 5.2 | 23 | 10,000 |
|  | 24 hr Flavourzyme | 100° F. |  | 23 | 10,000 |
| 1-2 | 24 hr Flavourzyme + 24 hr Fungal Protease 500,000 | Ambient | 4.8 | 33 | 13,000 |
|  | 24 hr Flavourzyme + 24 hr Fungal Protease 500,000 | 100° F. |  | 33 | 13,000 |

The following table gives the results of storing the samples at ambient temperature or in the incubator:

| Sample | Description | Temperature | 1 week | 2 weeks | 3 weeks |
|--------|-------------|-------------|--------|---------|---------|
| 1-0 | No enzyme | Ambient | Spoiled |  |  |
|  | No enzyme | 100° F. | Spoiled |  |  |
| 1-1 | Flavourzyme | Ambient | 15,000 | 20,000 | 20,000 |
|  | Flavourzyme | 100° F. | 12,000 | 10,000 | 8,000 |
| 1-2 | Flavourzyme + Fungal Protease 500,000 | Ambient | 10,000 | 15,000 | 12,000 |
|  | Flavourzyme + Fungal Protease 500,000 | 100° F. | 12,000 | 12,000 | 15,000 |

The experiments showed that there was bacteriostatic action after each digestion which did not seem to be dependent upon the temperature.

EXAMPLE 6

Various proteases were tested for suitability in digesting WPC. A master batch of 10 wt % solution of WPC 80 sold by LePrimo was prepared for the tests. Into 35 ml centrifuge tubes was placed 30 ml of the master batch and 0.3 ml of a 10 fold diluted protease. The centrifuge tubes were placed on a shaker in an oven at 110° F., shaken for 6 hours, removed, checked for pH and DH, and tasted by a trained human taster. The following table gives the results:

| Proteinase | Source | Supplier | pH | DH % | Flavor |
|------------|--------|----------|-----|------|--------|
| Flavourzyme | Fungal, *Aspergillus oryzae* | Novo | 5.6 | 8 | Acceptable |
| Fungal 500,000 | Fungal, *Aspergillus oryzae* | Genencor | 5.1 | 9 | Acceptable |
| Fungal Conc. | Fungal, *Aspergillus oryzae* | Genencor | 5.2 | 7 | Acceptable |
| Papain | Plant, papaya, fruit | Novo | 5.8 | 7 | ?? |
| Bromelain | Plant, pineapple, fruit | Novo | 5.8 | 6 | ?? |
| Ficin | Plant, fig, fruit | Novo | 5.8 | 5 | ?? |
| Pancreaatin | Animal, pancreas | Novo | 5.9 | 5 | ?? |
| Pepsin | Animal, stomach | Novo | 5.9 | 5 | ?? |
| Trypsin | Animal, pancreas | SCG | 5.9 | 5 | ?? |
| Protamex | Bacterial, Bacillus | Novo | 5.3 | 7 | Bitter |
| Alcalase | Bacterial, Bacillus | Novo | 5.0 | 10 | Bitter |
| Neutrase | Bacterial, *Bacillus subultis* | Novo | 5.3 | 8 | Bitter |
| Protex | Bacterial, *Bacillus lichenformis* | Genencor | 5.2 | 6 | Bitter |
| Novopro D | Bacterial, modified Bacillus | Novo | 5.3 | 8 | Bitter |
| APL | Bacterial, Bacillus | Altech | 5.1 | 8 | Bitter |

The experiments show that only the three fungal enzymes had an acceptable flavor. Of those three, Flavourzyme and Fungal Protease 500,000 had a higher DH %.

EXAMPLE 7

A batch of 400 ml of WPC 80 from LePrimo was prepared and divided into two parts. The temperature of the first part was raised to 110° F., 0.2 ml of Flavourzyme was added to it, and it was placed in an incubator and stirred. To the second part was added 0.2 ml of Flavourzyme and that part was placed in a forced air oven set at 125° F. After 24 hours the pH and DH were checked and a second amount of 0.2 ml Flavourzyme was added to each part. The following table gives the results:

| Sample | Description | Temperature (° F.) | Time | DH (%) | pH |
|--------|-------------|--------------------|------|--------|-----|
| A | Warm | 135 | 24 | 11 | 5.8 |
|  |  |  | 48 | 17 | 4.6 |
| B | SOP | 110 | 24 | 21 | 4.6 |
|  |  |  | 48 | 24 | 4.2 |

The experiment shows that 135° F. was too warm for Flavourzyme digestion of WPC.

EXAMPLE 8

Into a flask was placed 1 liter of warm water and 110 g of WP 80 from LePrimo, forming a 10 wt % solution. To the solution was added one ml of Flavourzyme and the temperature was raised to 110° F. Samples were taken at 12 hour intervals. At 24 hours a sample was taken to determine the heat coagulation temperature. Every 12 hours a 20 ml bacteriological sample was taken, split into two parts, and one part was evaluated for bacterial count as is and the other part was evaluated for bacterial count after pasteurization. The pasteurized sample was heated to 160° F. and was then stirred for 5 to 10 minutes. The following table gives the results:

| Sample | Time (hrs) | pH | DH (%) | Increase in DH %/hr | Taste | Count |
|---|---|---|---|---|---|---|
| 1 | 12 | 6.4 | 9 | 0.75 | Cheese | 20,000/ml |
| 2 | 24 | 5.8 | 14 | 0.4 | Cheese | 2000/ml |
| 2P | | | | | | 500,000/ml |
| 3 | 36 | 5.1 | 20 | 0.5 | Cheese | 500,000/ml |
| 4 | 48 | 4.8 | 26 | 0.5 | Cheese | 3000/ml |
| 5 | 60 | 4.7 | 28 | 0.15 | Cheese | 600,000/ml |
| 6 | 72 | 4.8 | 28 | none | Cheese | 1000/ml |

A second enzymatic digestion was started at 72 hrs with the addition of 1.0 g of Fungal Protease 500,000 to the batch:

| Sample | Time (hrs) | pH | DH (%) | Increase in DH %/hr | Taste | Count |
|---|---|---|---|---|---|---|
| 7 | 84 | 4.8 | 32 | 0.3 | Weak cheese | 20,000/ml |
| 8 | 95 | 4.8 | 36 | 0.3 | Cheese, weak fish | 2000/ml |

On each sample taken at 24 hours the temperature was raised to determine at what temperature the sample would begin to coagulate. It was determined that after 24 hrs the sample will begin to coagulate above 140° F., after 48 hrs at a DH of 30% the denaturation point was above 150° F., and after 72 hours the denaturation point was above 150° F. After completion of the experiment when the DH had risen to 35% the denaturation point was above 170° F. All the experiments on denaturation were performed with the solutions at a pH below 7. Two samples of the final product, one acid and one neutral, were permitted to stand overnight at ambient temperature. In both cases, a precipitate formed, but these samples had been brought to a boil after the determination of the drop out point. The experiments show that when the DH is higher the solution will withstand higher temperatures without heat denaturation of the larger peptides. The counts were fairly high, but there were no signs of spoilage.

EXAMPLE 9

In this Example, the effect on DH and the DH change per hour were determined by doubling three times the concentration of the enzyme using two of the better-performing proteases. Into 7 tubes was placed an amount of one of the enzymes and 30 ml of warm 10 wt % WPC 80 supplied by Davisco. The tubes were placed on a shaker and were shaken for 6 hours. The following table gives the results:

| Sample | Enzyme | Concentration (%) | pH | DH (%) |
|---|---|---|---|---|
| 1 | Alkalase | 0.1 | 5.6 | 20 |
| 2 | " | 0.2 | 5.6 | 19 |
| 3 | " | 0.3 | 5.4 | 25 |
| 4 | " | 0.4 | 5.5 | 27 |
| 5 | Flavourzyme | 0.1 | 5.6 | 21 |
| 6 | " | 0.2 | 5.6 | 23 |
| 7 | " | 0.4 | 5.6 | 21 |

There was a slight increase in DH with increase in concentration for Alcalase, but not for Flavorzyme. The very large increase in enzyme concentration did not significantly effect either the DH or the DH per hour. The pH's were also not effected by the changes in enzyme concentration during the digestion, which suggests that any level of enzyme over about 0.1% may not significantly improve the process.

What is claimed is:

1. A method of hydrolyzing a protein comprising
   (A) preparing an aqueous solution of said protein at a temperature of about 80 to about 125° F. and a concentration of about 5 to about 20 wt %, where said protein is from cow's milk and is selected from the group consisting of whey protein concentrate and casein;
   (B) digesting said aqueous solution with about 0.01 to about 1 wt % of a first fungal protease until the degree of hydrolyzation is about 16 to about 25%;
   (C) digesting said aqueous solution with about 0.01 to about 1 wt % of a second fungal protease until the degree of hydrolyzation is about 22 to about 40; and
   (D) evaporating water from said solution.
2. A method according to claim 1 wherein said first and second fungal proteases are from the fungus *Aspergillus oryzae*.
3. A method according to claim 1 wherein said water is evaporated by flash drying.
4. A method according to claim 1 including the additional step between steps (C) and (D) of mechanically deodorizing said product.
5. A method according to claim 1 wherein in step (D) some of the water is evaporated by heating and the remainder is evaporated by spray drying.
6. A method according to claim 1 wherein said protein is a soy product.
7. A method according to claim 1 wherein the pH of said solution is permitted to drift during steps (B) and (C).
8. A method according to claim 1 including the step of adjusting the pH, if necessary to about 6.5 to about 7.0 between steps (C) and (D).
9. A peptide product made according to the method of claim 1.
10. A food product containing a peptide product according to claim 8.
11. A milk replacement product comprising
    (A) about 4 to about 10 wt % of a carbohydrate;
    (B) about 1 to about 5 wt % of a fat; and
    (C) about 1 to about 5 wt % of a peptide product according to claim 8.
12. A method of hydrolyzing whey protein concentrate comprising
    (A) preparing an aqueous solution of said whey protein concentrate at a temperature of about 100 to about 115° F. and a concentration of about 8 to about 10 wt %;
    (B) digesting said aqueous solution with about 0.05 to about 0.3 wt % of a first fungal protease until the degree of hydrolyzation is about 20 to about 25%;
    (C) digesting said aqueous solution with about 0.05 to about 0.3 wt % of a second fungal protease until the degree of hydrolyzation is about 23 to about 35%;
    (D) adjusting the pH of said solution to between about 6.5 and about 7.0; and
    (E) evaporating water from said solution.
13. A peptide product made according to the method of claim 1.
14. A food product containing a peptide product according to claim 8.
15. A milk replacement product comprising
    (A) about 4 to about 10 wt % of a carbohydrate;
    (B) about 1 to about 5 wt % of a fat; and (C) about 1 to about 6 wt % of a peptide product according to claim 8.

16. A method of hydrolyzing whey protein concentrate comprising
   (A) preparing an aqueous solution of about 8 to about an 18 wt % whey protein concentrate from a whey protein concentrate that has a protein concentration of about 65 to about 80 wt %;
   (B) adding to said solution about 0.05 to about 0.3 wt % of a protease from the fungus *Aspergillus oryzae;*
   (C) heating said solution at a temperature of about 100 to about 115° F. until the degree of hydrolyzation is about 20 to about 25%;
   (D) adding to said solution about 0.05 to about 0.03 wt % of a protease from the fungus *Aspergillus oryzae;*
   (E) heating said solution at a temperature of about 100 to about 115° F. until the degree of hydrolyzation is about 23 to about 35%;
   (F) adjusting the pH of said solution to between about 6.5 and about 7.0; and
   (G) evaporating water from said solution.

17. A peptide product made according to the method of claim 16.

18. A milk replacement product comprising
   (A) about 4 to about 10 wt % of a carbohydrate;
   (B) about 1 to about 5 wt % of a fat; and
   (C) about 1 to about 6 wt % of a peptide product according to claim 17.

* * * * *